US009868120B2

(12) United States Patent
Boehm et al.

(10) Patent No.: US 9,868,120 B2
(45) Date of Patent: Jan. 16, 2018

(54) ROTATABLE CARTRIDGE WITH A METERING CHAMBER FOR ANALYZING A BIOLOGICAL SAMPLE

(71) Applicant: Roche Diagnostics Operations, Inc., Indianapolis, IN (US)

(72) Inventors: Christoph Boehm, Viernheim (DE); Sascha Lutz, Neustadt (DE); Juergen Spinke, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/352,680

(22) Filed: Nov. 16, 2016

(65) Prior Publication Data
US 2017/0095812 A1 Apr. 6, 2017

Related U.S. Application Data

(63) Continuation of application No. PCT/EP2015/063779, filed on Jun. 18, 2015.

(30) Foreign Application Priority Data
Jun. 6, 2014 (EP) .................................... 14171426

(51) Int. Cl.
B01L 3/00 (2006.01)
G01N 1/38 (2006.01)
(Continued)

(52) U.S. Cl.
CPC ..... B01L 3/50273 (2013.01); B01L 3/502738 (2013.01); G01N 1/38 (2013.01);
(Continued)

(58) Field of Classification Search
CPC ............. B01L 3/00; G01N 1/38; G01N 35/00
(Continued)

(56) References Cited

U.S. PATENT DOCUMENTS 4,284,602 A * 8/1981 Kelton .................. G01N 21/07 356/246
4,469,793 A * 9/1984 Guigan ................. B04B 5/0407 422/503
(Continued)

FOREIGN PATENT DOCUMENTS

EP 2302396 A1 3/2011

OTHER PUBLICATIONS

Kim et al., "Flow-enhanced electrochemical immunosensors on centrifugal microfluidic platforms", Lab on a Chip 13.18 2013; pp. 3747-3754, doi: 10.1039/c3lc50374g.
(Continued)

Primary Examiner — Arlen Soderquist
(74) Attorney, Agent, or Firm — Dinsmore & Shohl LLP

(57) ABSTRACT

An automatic analyzer cartridge, spinnable around a rotational axis, has aliquoting and metering chambers, a connecting duct there between, and a vent connected to the metering chamber and nearer to the rotational axis than the metering chamber. The metering chamber has side walls that taper away from a central region. Capillary action next to the side walls is greater than in the central region. A circular arc about the rotational axis passes through a duct entrance in the aliquoting chamber and a duct exit in the metering chamber. The cartridge has a downstream fluidic element which is part of a fluidic structure for processing a biological sample into the processed biological sample. A valve connects the metering chamber to the fluidic element, which is fluidically connected to the fluidic structure. The fluidic structure receives the biological sample and has a measurement structure for enabling measurement of the processed biological sample.

16 Claims, 8 Drawing Sheets

(51) Int. Cl.
*G01N 35/00* (2006.01)
*G01N 35/10* (2006.01)

(52) U.S. Cl.
CPC .............. *G01N 35/00069* (2013.01);
*B01L 2200/0684* (2013.01); *B01L 2200/10*
(2013.01); *B01L 2300/044* (2013.01); *B01L
2300/0672* (2013.01); *B01L 2300/0803*
(2013.01); *B01L 2300/087* (2013.01); *B01L
2400/0406* (2013.01); *B01L 2400/0409*
(2013.01); *B01L 2400/0688* (2013.01); *B01L
2400/0694* (2013.01); *G01N 2035/00257*
(2013.01); *G01N 2035/1032* (2013.01)

(58) Field of Classification Search
USPC .............................................. 422/72; 436/45
See application file for complete search history.

(56) References Cited

U.S. PATENT DOCUMENTS

| | | | | |
|---|---|---|---|---|
| 5,061,381 A * | 10/1991 | Burd | ...................... | G01N 21/07 422/72 |
| 5,089,417 A * | 2/1992 | Wogoman | ............. | B04B 5/0407 210/787 |
| 5,160,702 A * | 11/1992 | Kopf-Sill | .......... | B01L 3/502753 422/72 |
| 5,173,193 A * | 12/1992 | Schembri | ............... | G01N 21/07 422/72 |
| 5,173,262 A * | 12/1992 | Burtis | .............. | B01L 3/502753 422/50 |
| 5,186,844 A * | 2/1993 | Burd | ...................... | G01N 21/07 422/72 |
| 5,304,348 A * | 4/1994 | Burd | ...................... | G01N 21/07 422/72 |
| 5,591,643 A * | 1/1997 | Schembri | ............... | G01N 21/07 210/198.1 |
| 6,299,839 B1 * | 10/2001 | Karunaratne | ....... | B01F 13/0818 435/287.3 |
| 7,371,330 B2 * | 5/2008 | Ducree | ............. | B01L 3/502746 210/782 |
| 7,727,472 B2 * | 6/2010 | Nagaoka | ................ | G01N 21/07 422/50 |
| 7,938,030 B2 * | 5/2011 | Saiki | ...................... | B01L 3/5027 422/503 |
| 7,951,332 B2 * | 5/2011 | Cho | ................... | B01L 3/50273 422/502 |
| 7,972,577 B2 * | 7/2011 | Horiike | ............. | B01L 3/502746 422/50 |
| 8,048,387 B2 * | 11/2011 | Lee | ..................... | B01L 3/50273 422/502 |
| 8,114,351 B2 | 2/2012 | Degenhardt | | |
| 8,440,147 B2 * | 5/2013 | Garcia Da Fonseca | .......................... | B01L 3/50273 422/50 |
| 8,470,588 B2 * | 6/2013 | Boehm | ................ | B01L 3/5023 422/414 |
| 8,796,029 B2 * | 8/2014 | Chung | ............. | B01L 3/502738 422/64 |
| 8,911,684 B2 * | 12/2014 | Augstein | ............... | B01F 1/0027 422/50 |
| 8,956,580 B2 * | 2/2015 | Lai | ......................... | B01L 3/508 422/415 |
| 9,012,228 B2 * | 4/2015 | Kim | ..................... | G01N 33/491 422/502 |
| 9,151,750 B2 * | 10/2015 | Boehm | ............. | B01L 3/502753 |
| 9,186,671 B2 * | 11/2015 | Augstein | .......... | B01L 3/502723 |
| 9,221,051 B2 * | 12/2015 | Boehm | ............. | B01L 3/502738 |
| 9,417,164 B2 * | 8/2016 | Boehm | ................. | B01F 1/0022 |
| 2002/0106786 A1 * | 8/2002 | Carvalho | ............. | B01F 5/0647 422/72 |
| 2003/0053934 A1 * | 3/2003 | Andersson | ............ | B01F 5/0646 422/72 |
| 2008/0035579 A1 * | 2/2008 | Lee | ................... | B01L 3/502761 210/695 |
| 2008/0058991 A1 * | 3/2008 | Lee | ....................... | B01L 3/5027 700/266 |
| 2008/0108120 A1 * | 5/2008 | Cho | ..................... | B01F 13/0059 435/173.7 |
| 2009/0053108 A1 * | 2/2009 | Cho | ................... | B01L 3/502753 422/72 |
| 2009/0155925 A1 * | 6/2009 | Boehm | ................. | B01F 1/0022 436/174 |
| 2009/0169430 A1 * | 7/2009 | Yamamoto | .......... | B01L 3/50273 422/72 |
| 2009/0191643 A1 * | 7/2009 | Boehm | ................. | B01L 3/5023 436/164 |
| 2009/0246082 A1 | 10/2009 | Saiki et al. | | |
| 2009/0317896 A1 * | 12/2009 | Yoo | ................... | B01L 3/502738 435/287.1 |
| 2010/0158757 A1 * | 6/2010 | Horiike | ............. | B01L 3/502746 422/72 |
| 2011/0053202 A1 * | 3/2011 | Parng | ................ | B01L 3/502746 435/29 |
| 2011/0201101 A1 * | 8/2011 | Lee | ..................... | B01L 3/50273 435/288.7 |
| 2011/0263030 A1 * | 10/2011 | Kim | .................... | B01L 3/50273 436/45 |
| 2012/0301371 A1 * | 11/2012 | Augstein | ............... | B01F 1/0027 422/502 |
| 2013/0004964 A1 * | 1/2013 | Boehm | ................ | B01L 3/502753 435/7.4 |
| 2013/0196447 A1 * | 8/2013 | Boehm | ................ | B01F 1/0022 436/166 |
| 2013/0236376 A1 * | 9/2013 | Augstein | ........... | B01L 3/502723 422/506 |
| 2013/0243664 A1 * | 9/2013 | Boehm | ................ | B01L 3/502738 422/504 |
| 2014/0309555 A1 * | 10/2014 | Gelfand | ........... | A61B 5/150305 600/583 |
| 2016/0320274 A1 * | 11/2016 | Boehm | ................. | B01F 1/0022 |
| 2017/0095811 A1 * | 4/2017 | Boehm | ................. | B01L 3/502723 |
| 2017/0095813 A1 * | 4/2017 | Boehm | ................. | G01N 35/00069 |
| 2017/0095814 A1 * | 4/2017 | Boehm | ................. | B01L 3/50273 |

OTHER PUBLICATIONS

Martinez-Duarte et al., "The integration of 3D carbon-electrode dielectrophoresis on a CD-like centrifugal microfluidic platform", Lab on a Chip 10.8, 2010; pp. 1030-1043, doi: 10.1039/B925456K.
Park et al., "Multifunctional microvalves control by optical illumination on nanoheaters and its application in centrifugal microfluidic devices", Lab Chip, 2007, 7, pp. 557-564.

* cited by examiner

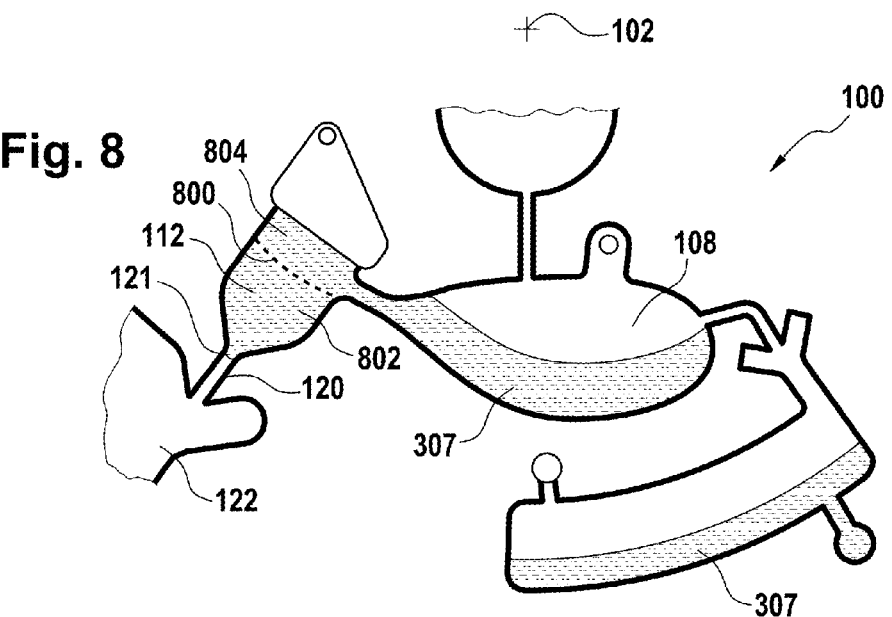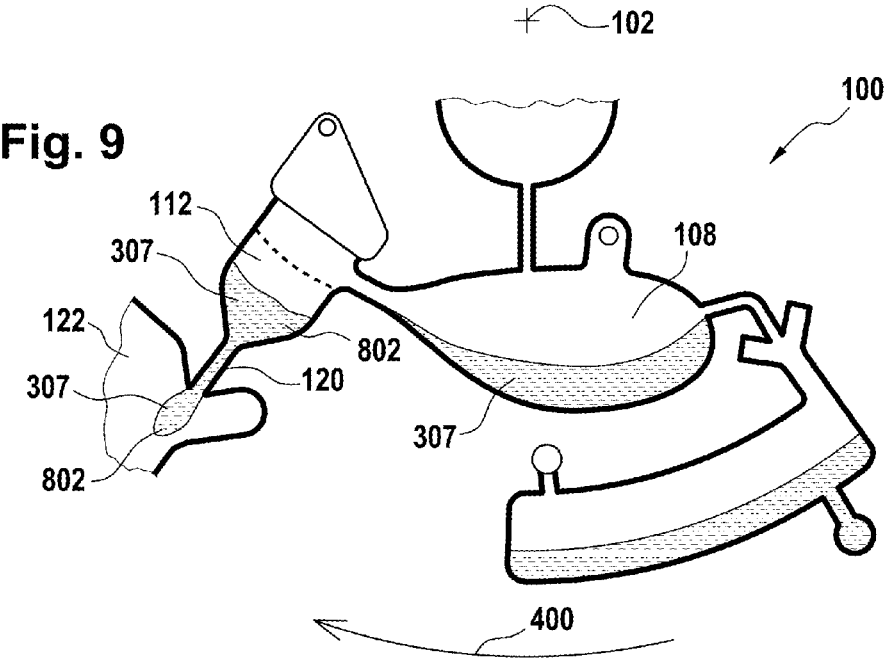

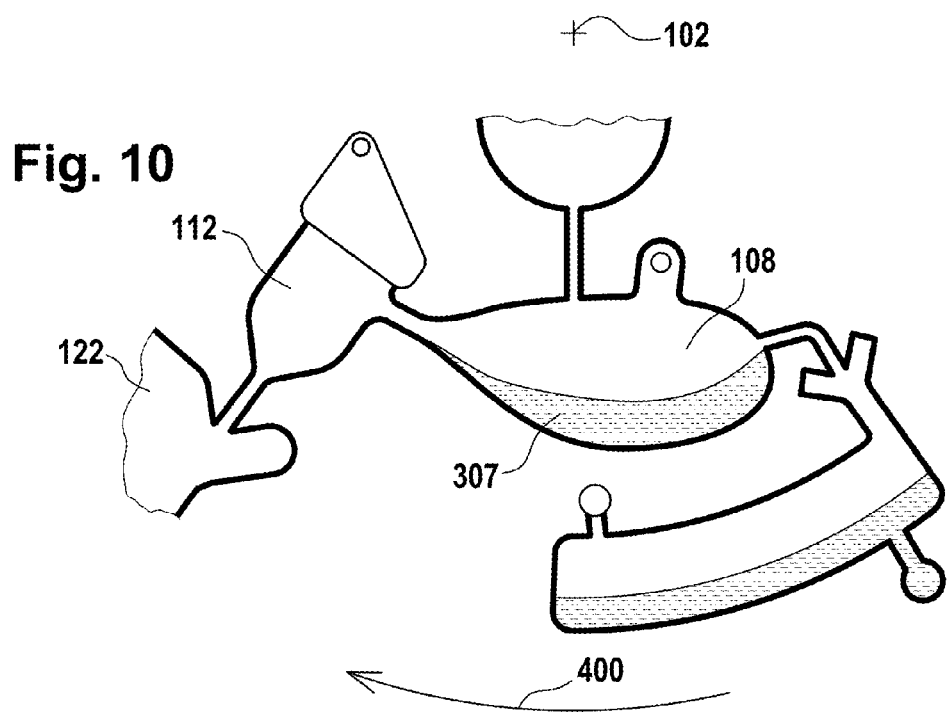

ROTATABLE CARTRIDGE WITH A METERING CHAMBER FOR ANALYZING A BIOLOGICAL SAMPLE

CROSS-REFERENCE TO RELATED APPLICATIONS

This application is a continuation of International Application No. PCT/EP2015/063779 filed Jun. 18, 2015, which claims priority to European patent application No. EP14171426.1, filed Jun. 6, 2014.

TECHNICAL FIELD

The inventive embodiments disclosed herein relate to analytical test devices for biological samples, in particular to the design and use of rotatable cartridges for performing a measurement of a biological sample.

BACKGROUND AND RELATED ART

Two classes of analysis systems are known in the field of medical analysis: wet analysis systems, and dry-chemical analysis systems. Wet analysis systems, which essentially operate using "wet reagents" (liquid reagents), perform an analysis via a number of required step such as, for example, providing a sample and a reagent into a reagent vessel, mixing the sample and reagent together in the reagent vessel, and measuring and analyzing the mixture for a measurement variable characteristic to provide a desired analytical result (analysis result). Such steps are often performed using technically complex, large, line-operated analysis instruments, which allow manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and dissolved reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, and some of them are portable and battery-operated. The systems are used for decentralized analysis, for example, at resident physicians, on the wards of the hospitals, and in so-called "home monitoring" during the monitoring of medical-analytic parameters by the patient himself (in particular blood glucose analysis by diabetics or coagulation status by warfarin patients).

In wet analysis systems, the high-performance analysis instruments allow the performance of more complex multi-step reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the probe can first be transported through a porous solid matrix, which contains a specific binding reagent for the analyte. A marking reagent can subsequently be caused to flow through the porous matrix, to mark the bound analyte and allow its detection. To achieve precise analysis, a washing step must be performed, in which unbound marking reagent is completely removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control is especially frequently performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping. Microstructures, which are generated by lithography methods, increasingly being used more recently, however.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

U.S. Pat. No. 8,114,351 B2 discloses an analysis system for the analysis of a body fluid sample for an analyte. The analysis system provides a test element and an analysis instrument having a dosing station and a measurement station. The test element has a housing an (at least) one sample analysis channel enclosed by the housing. The test element is rotatable around an axis of rotation which extends through the test element.

U.S. Pat. No. 8,470,588 B2 discloses a test element and a method for detecting an analyte. The test element is essentially disk shaped and flat, and can be rotated about a preferably central axis which is perpendicular to the plane of the disk shaped test element.

Kim, Tae-Hyeong, et al. "Flow-enhanced electrochemical immunosensors on centrifugal microfluidic platforms." Lab on a Chip 13.18 (2013): 3747-3754, doi:10.1039/c3lc50374g, (hereafter "Kim et. al.") discloses a fully integrated centrifugal microfluidic device with features for target antigen capture from biological samples, via a bead-based enzyme-linked immune-sorbent assay, and flow-enhanced electrochemical detection. This is integrated into a Centrifugal microfluidic discs, also known as "lab-on-a-disc" or microfluidic CDs.

Martinez-Duarte, Rodrigo, et al. "The integration of 3D carbon-electrode dielectrophoresis on a CD-like centrifugal microfluidic platform." Lab on a Chip 10.8 (2010): 1030-1043, doi:10.1039/B925456K, (hereafter "Martinez-Duarte et. al.") discloses a dielectrophoresis (DEP)-assisted filter with a compact disk (CD)-based centrifugal platform. 3D carbon electrodes are fabricated using the C-MEMS technique and are used to implement a DEP-enabled active filter to trap particles of interest.

European patent application publication EP 2 302 396 A1 discloses an analyzing device includes: an operation cavity that is adjacent to a first reserving cavity retaining a sample liquid, in a circumferential direction of rotational driving; a connecting section provided on a side wall of the first reserving cavity to suck the sample liquid by a capillary force and transfer the sample liquid to the operation cavity; and second reserving cavities that are disposed outside the operation cavity in the circumferential direction of the rotational driving and communicate with the outermost position of the operation cavity through a connecting passage. The connecting section is circumferentially extended farther than the liquid level of the sample liquid retained in the first reserving cavity.

United States patent application publication US 2009/0246082 discloses an analysis device comprising a separation chamber for separating a sample solution into a solution component and a solid component, a holding channel for holding a predetermined amount of the separated solid component, a mixing chamber connected to the holding channel, an overflow channel connected between the holding channel and the separation chamber, a sample overflow chamber into which the sample solution remaining in the separation chamber is discharged, and a joint channel connecting the separation chamber and the sample overflow chamber. After the separated solution component fills the overflow channel with priority by a capillary force, the separated solid component is transferred to the holding channel via the overflow channel, and a predetermined amount of the solid component is measured. The solid component in the holding channel is transferred to the mixing chamber by a centrifugal force, and simultaneously, the sample solution remaining in the separation chamber is discharged to the sample overflow chamber by the siphon effect of the joint channel.

SUMMARY

A method of performing a measurement on a processed biological sample using the cartridge, a cartridge for an automatic analyzer, and an automatic analyzer are disclosed in the independent claims. Additional embodiments are given in the dependent claims.

In one aspect of the invention, an embodiment provides for a method of performing a measurement of a processed biological sample using a cartridge.

A cartridge as used here encompasses also any test element for processing the biological sample into a processed biological sample. The cartridge may include structures or components which enable a measurement to be performed on the biological sample. A cartridge is a test element as is defined and explained in U.S. Pat. Nos. 8,114,351 B2 and 8,470,588 B2. A cartridge as used herein may also be referred to as a Centrifugal microfluidic disc, also known as "lab-on-a-disc" or a microfluidic CD.

A biological sample as used herein encompasses as chemical product derived, copied, replicated, or reproduced from a sample taken from an organism.

The cartridge is operable for being spun around a rotational axis. The cartridge comprises an aliquoting chamber. The cartridge further comprises a metering chamber. The cartridge further comprises a connecting duct for connecting the metering chamber with the aliquoting chamber. The connecting duct comprises a duct entrance in the aliquoting chamber. The connecting duct further comprises a duct exit in the metering chamber. A circular arc about or drawn about the rotational axis would pass through both the duct entrance and the duct exit. An equivalent statement would be that connecting the duct exit and the duct entrance are roughly or approximately equidistant to the rotational axis.

The cartridge further comprises a downstream fluidic element. The downstream fluidic element is connected to the metering chamber via a valve. The downstream fluidic element is downstream to the metering chamber. There is a flow of fluid from the metering chamber to the downstream fluidic element.

The cartridge further comprises a fluidic structure for processing a biological sample into the processed biological sample. The fluidic structure comprises the downstream fluidic element. The downstream fluidic element is fluidically connected to the fluidic structure. The downstream fluidic element is a component or a part of the fluidic structure. The fluidic structure comprises a measurement structure for enabling measurement of the processed biological sample. The fluidic structure is configured for receiving the biological sample. For instance the cartridge may have an entrance receptacle adapted for receiving the biological sample.

The method comprises the step of placing the biological sample into the fluidic structure. The method further comprises the step of controlling the rotational rate of the cartridge to process the biological sample into the processed biological sample using the fluidic structure. The method further comprises filling the aliquoting chamber with a fluid. In some examples the aliquoting chamber has fluid added directly to it, for example with a pipette or other dispenser. In other embodiments there is a reservoir which opens into the aliquoting chamber. In yet other embodiments there may be another container or reservoir within the cartridge that contains the fluid and then this fluid is emptied or dispensed into the aliquoting chamber. The method further comprises the step of decreasing the rotational rate of the cartridge to permit or force the fluid in the aliquoting chamber to flow into the connecting duct and to fill the metering chamber for a first time. The decrease in the rotational rate of the cartridge may cause the fluid to move within the aliquoting chamber. For instance a rapid deceleration of the fluid may be used to splash the fluid in the direction of the connecting duct.

The method further comprises increasing the rotational rate of the cartridge to transfer a first part of the fluid from the metering chamber through the valve and to transfer a first remaining part back into the aliquoting chamber. In some examples the fluid may be drawn into the metering chamber by capillary forces. The decrease in the rotational rate may cause the fluid to splash or move against the connecting duct and then the capillary forces may then fill the metering chamber. Increasing the rotational rate of the cartridge to transfer the first part of the fluid may have the effect of also cancelling any capillary forces which are drawing fluid into the metering chamber.

The method further comprises the step of decreasing the rotational rate of cartridge to permit or force the fluid in the reservoir to flow into the metering chamber and to fill the metering chamber a second time. This is a repetition of the second to last step. The method further comprises increasing the rotational rate of the cartridge to transfer a second part of the fluid from the metering chamber through the valve and to transfer a second remaining part back into the aliquoting chamber. This and the subsequent steps illustrate that the metering chamber and aliquoting chamber may be used to fill and empty the metering chamber multiple times and thereby provide fluid parts multiple times to the downstream fluidic element.

And finally the method comprises performing the measurement using the measurement structure and using a measurement system. This method may have the advantage that the fluid can be transferred from the aliquoting chamber multiple times to the downstream fluidic element. In some examples the measurement is an optical measurement. The measurement may include, but is not limited to: a photometric transmission measurement, a measurement of the scattering of light, a chemiluminescence, a fluorescence, and electrochemiluminescense (ECL) measurement.

In some examples the first part of the fluid and the second part of the fluid have the same volume. In further embodiments the first remaining part and the second remaining part both have the same volume.

It should be noted that the aliquoting chamber and metering chamber described above may be used to dispense a part of the fluid multiple numbers of times.

In one example the aliquoting chamber has a depth of approximately 2.5 mm and a width of 4.0 mm. The height in the radial direction (towards the axis of rotation) may be 7 mm.

In one example the metering chamber may have depth of 0.8 mm and a width of 3.5 mm. The height without the expansion chamber may be approximately 7.0 mm.

In another embodiment, the metering chamber has side walls and a central region. The side walls taper away from the central region. Capillary action next to the side walls of the metering chamber is greater than in the central region of the metering chamber.

In another embodiment the cartridge further comprises a vent which is connected to the metering chamber. The vent is nearer to the rotational axis than the metering chamber. The vent for example may be connected such that gas is able to enter or exit the metering chamber. This may enable fluid to enter or exit the metering chamber.

In another embodiment, the cartridge further comprises an expansion chamber with a vent. The expansion chamber is connected to the metering chamber. The capillary action in the metering chamber is greater than capillary action in the expansion chamber. The expansion chamber is nearer to the rotational axis than the metering chamber In another embodiment the interface between the metering chamber and the expansion chamber is formed as a capillary valve or a capillary stop valve. In this embodiment the cross section of the metering chamber increases step like towards the larger cross section of the expansion chamber. Thereby the fluid will not flow from the metering chamber into the expansion chamber if no additional forces are applied.

The expansion chamber is nearer to the rotational axis than the metering chamber Capillary action as used herein may also refer to capillarity, capillary motion, or wicking, or capillary force. Capillary action is the ability of a liquid to flow in narrow spaces without the assistance of external forces like gravity or centrifugal forces.

Capillary action is caused by intermolecular forces between the liquid and adjacent solid surfaces. Adhesive forces between the liquid and the adjacent solid surfaces can be used to counteract gravity or other external forces. In some cases the capillary action can be increased by decreasing the distance between adjacent solid surfaces.

This embodiment may have the advantage that the metering chamber fills first at the side walls surrounding the central region and thereafter at the central region. This fills the metering chamber in a predictable and controllable way that reduces the chances that bubbles will form or adhere.

The formation of bubbles prevent most microfluidic structures from being used more than once for dispensing a metered amount of fluid. For example, the patent application US 2009/0246082 A1 teaches the use of air holes which are positioned in various locations in an overflow chamber or channel. See for example FIGS. 3, 4, and 5 of US 2009/0246082 A1. The chamber of 13 of FIG. 5(a) is essentially a siphon. The positioning of an air hole at the bend of a siphons as is depicted in FIG. 5(a) however does not enable the repeatable aliquoting of fluid in the way that having a metering camber with side walls and a central region as described above. This potential advantage is described in greater detail below.

Similarly an aliquoting structure described in EP 2302396 A1 enables parallel splitting of fluid in several aliquots, but also uses a venting structure that only lets air in at the position nearest to the rotational axis. For example see FIG. 55 of EP 2302396 A1 and the accompanying text. The structure shown in the picture features a long capillary channel that has to be filled by fluid. The channel features several vents and connections to downstream chambers.

In FIG. 42, of EP 2302396 A1 a siphon 215b connects a chamber 210b with another chamber 209c. Placing a vent at the point of siphon 215b closest to the rotational axis 107 would not enable the reliable aliquotation of the same amount of fluid every time due to the risk of bubble formation. The structures shown in EP 2302396 has the following drawbacks: The refilling of such a structure for a second aliquoting step is highly unreliable. For a second aliquoting step the capillary has to be filled again. As the walls of the capillary are still wetted the filling process differs from the initial filling process of the first aliquoting step. The fluid moves significantly faster along the channel walls than along the channels center. Due to the small channel diameter fluid progressing on one channel wall often gets in contact with fluid the other channel wall. This causes the formation of an air bubble that clogs the channel. This effect is significantly increased if fluids with low surface tension (e.g. washing buffers) are aliquoted. The probability of air bubble formation rises with the length of the capillary to be filled.

Experiments conducted show that long capillaries cannot be reliably used in repetitive aliquoting steps. A structure with a single long capillary and a vent near the bend was constructed. During the tests air bubbles clogged the vent consistently when a second aliquotation of the liquid is attempted.

The present embodiment may have a further advantage by that enables serial and accurate aliquoting steps. A "closed" capillary with four walls can be completely avoided in this structure. In some examples, the fluid may pass the second duct and reach the metering chamber due to the inertia of the fluid by stopping the rotation of the disk with a negative acceleration. In some examples, the second duct does not act as capillary. In some embodiments, the fluid may pass the second duct and reach the metering chamber due both capillary forces and forces caused by inertia. In the metering chamber the side walls may function as guidance structures at the outer walls guide the fluid due to a higher capillary action than the central region. After the side walls have filled, the central part of the metering chamber may also fill by capillary forces. The guidance structure features a "open" capillary structure comprising three walls preventing air bubble formation or adhesion. The edge of the metering chamber closest to the rotational axis borders an expansion chamber. In some examples the central part of the metering chamber borders the expansion chamber over its whole width. This may avoid or reduce the risk of air bubble formation in the metering chamber which may enable the precise metering and reliable refilling of the metering chamber for multiple subsequent aliquotations using the same microfluidic structure.

This structure enabled serial aliquoting of three aliquots in 8/8 tested disks.

In addition to the potential advantages describe above, the fluidic structure in US 2009/0246082 has the additional disadvantage when compared to the present embodiment. The overflow chamber 15 (see FIG. 5(c) of US 2009/0246082) serves to maintain and hold surplus fluid which is in contrast to the present embodiment. Surplus fluid will become trapped in the overflow chamber 15. In the present embodiment, the fluid in the aliquoting chamber may be able to be transferred to the metering chamber.

In another embodiment the direction of the rotation of the cartridge is such that the direction of rotation passes through the aliquoting chamber first then the metering chamber. This has the effect that when the cartridge is decelerated the fluid is forced up to the connecting duct.

In another embodiment the connecting duct is a funnel which serves to funnel fluid from the aliquoting chamber to the metering chamber.

In another embodiment the rotational axis of the cartridge is vertical when the method is performed.

In another embodiment, the side walls of the metering chamber border the expansion chamber.

In another embodiment, the side walls has a region closest to the rotational axis wherein the region borders to and opens into the expansion chamber.

In another embodiment, the central region of the metering chamber borders the expansion chamber.

In another embodiment, the central region has a zone closest to the rotational axis. wherein the region borders to and opens into the expansion chamber.

In another embodiment, the measuring chamber has a border between the metering chamber and the expansion chamber. The border is at least 5 time longer than the width of the valve.

In another embodiment the valve is a capillary valve or a capillary stop valve.

A capillary valve or capillary stop value as used herein is a valve or structure which uses the capillary force of a fluid to prevent fluid from flowing through the capillary stop valve. For example a tube with a sufficiently small diameter will draw fluid into it and the capillary force will prevent the fluid from flowing out of the tube. For the case of this tube the entrance and exit of the tube function as capillary stop valves. In some examples the duct exit itself may have dimensions small enough (compared to the adjacent fluidic structures and chambers) that the duct exit functions as a capillary stop.

In another embodiment the valve is a microvalve which is able to be opened and resealed. For example a paraffin-based valve with an embedded micro-heater may be used.

In another example the microvalve may be a valve based on a ferrofluid such as is described in Park et al in the article "Multifunctional Microvalves Control by Optical Illumination on Nanoheaters and Its Application in Centrifugal Microfluidic Devices" in Lab Chip, 2007, 7, pages 557-564.

In another embodiment the fluidic structure is a microfluidic structure.

In another embodiment the step of increasing the rotational rate of the cartridge to transfer a first part of the fluid from the metering chamber through the valve comprises increasing the rotational rate of the cartridge to a first rotational rate to transfer the remaining part of the fluid back to the aliquoting chamber and increasing the rotational rate of the cartridge to a second rotational rate to transfer the first part of the fluid from the metering chamber through the valve. When the cartridge is rotated at a higher rate at the first rotational rate the centrifugal force becomes greater than any capillary force which is drawing fluid into the metering chamber. Fluid is then forced out of the metering chamber until the fluid level is equal with the lowest level of the duct exit. Increasing to the second rotational rate then forces the fluid through the valve. In some examples the valve is open. For example if a ferrofluid or a paraffin-based microvalve is used.

This embodiment may have the benefit of increasing the accuracy of the fluid which is dispensed to the downstream fluidic element. As an alternative to this the cartridge is simply rotated at a rate which is fast enough to force the fluid through the valve. This may result in the amount of fluid being transferred to the downstream fluidic element if the first and second rotational rates are used. In another alternative if the valve is a controllably sealable or openable microvalve then the cartridge may be operated at a rotational rate to force the remaining part of the fluid back into the aliquoting chamber. After this is accomplished then the microvalve is opened and the rotation forces the fluid from the metering chamber into the downstream fluidic element. As an alternative it may be possible to replace the microvalve with a reusable siphon.

In another embodiment the step of increasing the rotational rate of the cartridge to transfer a second part of the fluid from the metering chamber through the valve comprises increasing the rotational rate of the cartridge to the first rotational rate to transfer the remaining part of the fluid back to the aliquoting chamber and increasing the rotational rate of the cartridge to the second rotational rate to transfer the second part of the fluid from the metering chamber through the valve.

In another embodiment the cartridge further comprises a fluid chamber for receiving a fluid. The cartridge further comprises a fluid chamber duct connecting the fluid chamber and the aliquoting chamber. Filling the aliquoting chamber comprises filling the fluid chamber with the fluid. Filling the aliquoting chamber further comprises controlling the rotational rate of the cartridge to transport the fluid from the fluid chamber to the aliquoting chamber via the fluid chamber duct.

In another aspect the invention, an embodiment provides for a cartridge for an automatic analyzer. The cartridge is operable for being spun around a rotational axis. The cartridge comprises an aliquoting chamber. The cartridge further comprises a metering chamber. The cartridge further comprises a connecting duct for connecting the metering chamber with the aliquoting chamber. The connecting duct comprises a duct entrance in the aliquoting chamber. The connecting duct further comprises a duct exit in the metering chamber. A circular arc about the rotational axis passes through both the duct entrance and the duct exit. The cartridge further comprises a downstream fluidic element. The downstream fluidic element is connected to the metering chamber via a valve. The cartridge further comprises a fluidic structure for processing a biological sample into the processed biological sample. The fluidic structure comprises the downstream fluidic element. The downstream fluidic element is fluidically connected to the fluidic structure. The fluidic structure comprises a measurement structure for enabling measurement of the processed biological sample. The fluidic structure is configured for receiving the biological sample.

In another embodiment the cartridge further comprises an excess fluid chamber connected to the aliquoting chamber via a fluidic connection. The fluidic connection comprises a fluidic connection entrance. The fluidic connection entrance is further away from the rotational axis than the circular arc that passes through both the duct entrance and the duct exit. The fluidic connection entrance sets the maximum level of the fluid in the aliquoting chamber. The statement that the fluidic connection entrance is further away from the rotational axis than the circular arc that passes through both the duct entrance and the duct exit is equivalent to stating that the duct entrance is above the maximum fluid level in the aliquoting chamber. When the cartridge is rotating at a sufficiently large rotational rate the centrifugal force will keep the fluid in the aliquoting chamber and the maximum level will be set by the fluidic connection entrance. Slowing the rate of the rotation may cause the inertia of the fluid to cause it to move towards the duct entrance. This may then result in fluid being transferred to the metering chamber.

In another embodiment the aliquoting chamber has a lower portion and an upper portion. The lower portion is further from the rotational axis than the upper portion. A cross-sectional profile of the lower portion tapers away from the upper portion. In an embodiment the lower portion is defined by the duct entrance and its entry into the aliquoting chamber. Having the lower portion taper away from the upper portion means that the lower portion becomes more narrow as the distance from the rotational axis increases. This narrowing or tapering may be used to increase the capillary force in the lower portion. The lower portion may also extend up to the connecting duct. This may provide a way for capillary forces to direct fluid towards the metering chamber.

In another embodiment the lower portion is operable for causing fluid to flow into the connecting duct using capillary action. The taper may cause capillary forces. This may be used to direct fluid to the connecting duct and thus ultimately to the metering chamber.

In another embodiment the connecting duct is operable for causing fluid to flow from the aliquoting chamber to the metering chamber using inertia and capillary forces.

In another embodiment the aliquoting chamber has sidewalls. The sidewall located next to the metering chamber may have a tapered profile to create a capillary force which sucks or draws fluid into this area and assists in transporting fluid to the connecting duct and thus to the metering chamber.

In another embodiment the metering chamber has a metering chamber surface. A part of the metering chamber surface is rounded.

In another embodiment the entire surface of the metering chamber is rounded. It may be beneficial to have the surfaces of the metering surface rounded so that there are no sharp corners. This may help to effectively transfer fluid to the metering chamber and to fill the metering chamber completely. For instance corners and other such areas with narrow areas may trap bubbles. Having bubbles trapped in the metering chamber will effectively change the volume that the metering chamber is able to transfer. Having a different number of bubbles or bubbles with different volumes at different times may result in an inconsistent amount of fluid being transferred by the metering chamber to the downstream fluidic element. Using these smooth surfaces within the metering chamber reduces the chances of bubbles thus providing for more consistent transfer of fluid to the downstream fluidic element.

In another embodiment the metering chamber has sidewalls and a central region. The sidewalls taper away from the central region. Having the sidewalls taper away from the central region may result in a larger capillary action near the sidewalls than in the central region area. This may cause the sidewalls to fill first with fluid and this may reduce the chances of bubbles forming or adhering in the metering chamber.

In other embodiments the metering chamber has sidewalls. A profile of the metering chamber tapers towards the sidewalls.

In another embodiment the capillary action next to the sidewalls of the metering chamber is greater than the capillary action in the central region of the metering chamber. This may result in the sidewalls filling with fluid before the central region.

In another embodiment the sidewalls are operable for filling with fluid before the central region to prevent the formation and/or adherence of bubbles in the metering chamber.

In another embodiment the metering chamber is operable for causing fluid to fill the metering chamber using capillary action.

In another embodiment the connecting duct is operable for causing fluid to flow from the aliquoting chamber to the metering chamber using capillary action.

For example the connecting duct may have a depth 0.5 mm and a width in the radial direction of 1 mm. The depth may also be greater than 0.2 mm. The width may also be greater than 0.2 mm.

In another embodiment the capillary action in the metering chamber is greater than the capillary action in the connecting duct.

In another embodiment the capillary action in the connecting duct is higher than the capillary action in the aliquoting chamber in particular the lower portion of the aliquoting chamber.

In another embodiment the capillary action in the connecting duct is higher than the capillary action in the lower portion of the aliquoting chamber and the capillary action in the lower portion of the aliquoting chamber is higher than the capillary action in the upper portion of the aliquoting chamber.

In another embodiment the cartridge further comprises an expansion chamber with a vent. The expansion chamber is fluidically connected to the metering chamber. The capillary action in the metering chamber is greater than the capillary action in the expansion chamber. The expansion chamber is nearer to the rotational axis than the metering chamber. The use of such an expansion chamber may allow air to uniformly exit the metering chamber. This may further reduce the chances of bubbles forming or adhering in the metering chamber.

In another embodiment the metering chamber has an upper edge or surface. The upper edge or surface is the boundary of the metering chamber that is closer to the rotational axis than the rest of the metering chamber. In this embodiment the whole upper section or boundary of the metering chamber may open into the expansion chamber. This may further reduce the chances of bubbles forming or adhering when filling the metering chamber.

In another embodiment the cartridge further comprises a fluid chamber for receiving a fluid. The cartridge further comprises a fluid chamber duct connecting the fluid chamber and the aliquoting chamber.

In another embodiment the cartridge further comprises a reservoir filled with the fluid. The reservoir is configured for being opened and for transferring the fluid to the fluid chamber. The cartridge may have for example a reservoir opening element that could be used for opening the reservoir. It may also be possible that an actuator could be used to actuate or activate the reservoir opening element. For instance an automatic analyzer may have a device which would cause the actuation of the reservoir or a mechanism attached to it in order to open the reservoir allowing the fluid contained in the reservoir to be entered into the fluid chamber.

The reservoir may for example be sealed with a removable or pierceable seal that could for example be a thin film or a foil. For example a small piece of metal foil or a thin film of plastic may be used as a pierceable seal. The fluid chamber or another component of the cartridge may have a piercing structure for opening the pierceable seal. The piercing structure may be any structure which is capable of piercing the particular pierceable seal and for instance could be a pin, a lance, or a sharp edge. In other examples the removable seal may be able to be peeled off to open the reservoir.

In another embodiment the fluid chamber or a fluid receiving structure connected to the fluid chamber is configured for receiving a dosing needle for dispensing the fluid to the fluid chamber. This for instance may be performed manually or an automatic analyzer may have a dosing needle which automatically dispenses fluid to the fluid chamber or the fluid receiving structure.

In another embodiment the fluid is any one of the following: a dispersion, a fluid comprising nanoparticles, a fluid comprising a blood grouping reagent, a fluid comprising an immune reagent, a fluid comprising an antibody, a fluid comprising an enzyme, a fluid comprising one or more substrates for an enzymatic reaction, a fluid comprising fluorescence emitting molecules, a fluid comprising molecules for measuring immunochemical reactions, a fluid comprising molecules for measuring reactions of nucleic acids, a fluid comprising a recombinant protein, a fluid comprising virus isolate, a fluid comprising a virus, a fluid comprising a biological reagent, a solvent, a diluent, a buffer, a fluid comprising a protein, a fluid comprising a salt, a detergent, a fluid comprising a fluid comprising a nucleic acid, a fluid comprising an acid, a fluid comprising a base, an aqueous solution, a non-aqueous solution, and combinations thereof.

In another embodiment the measurement structure comprises two or more electrodes and/or an optical measurement structure. The measurement system comprises a system for making an electrical measurement. The measurement system comprises a system for making optical measurements.

In some embodiments the optical measurement structure may be a transparent structure or an optically transparent structure. The measurement system comprises an optical measurement system.

In some examples optically transparent may include near infrared and near ultraviolet. In other examples optically transparent may exclude the near infrared or near ultraviolet.

Some examples may have both the measurement structure with the transparent structure and also the electrodes for more complicated tests. For example the measurement structure may be a structure for making electrochemiluminescence measurements where electrodes cause an optical excitation in a sample.

In other examples the measurement structure comprises two or more electrodes for making an electrical measurement or ECL measurement of the processed biological sample. For example the measurement structures of Martinez-Duarte et. al. or Kim et. al. may be incorporated into a cartridge.

Examples may also only have electrode. For example in an electrochemical detection structure an electrode may be used to measure a current caused by the result of a enzymatic reaction.

In another aspect of the invention, an embodiment provides for an automatic analyzer configured for receiving a cartridge according to an embodiment. The automatic analyzer comprises a cartridge spinner, a measurement system, and a controller configured to control the automatic analyzer. The cartridge spinner may be adapted for spinning the cartridge about the rotational axis.

The controller is configured or programmed to control the cartridge spinner to control the rotational rate of the cartridge to process the biological sample into the processed biological sample using the fluidic structure. This may involve rotating the cartridge at different rates for varying amounts of time to process the biological sample into the processed biological sample using the fluidic structure. The controller is further configured or programmed to control the cartridge spinner to decrease the rotational rate of the cartridge to force the fluid in the reservoir into the connecting duct and to fill the metering chamber a first time. The controller is further configured or programmed to control the cartridge spinner to increase the rotational rate of the cartridge to transfer a first part of the fluid from the metering chamber through a valve and to transfer a first remaining part back into the aliquoting chamber.

The controller is further configured or programmed to control the cartridge spinner to decrease the rotational rate of the cartridge to force the fluid in the reservoir into the connecting duct and to fill the metering chamber a second time. The controller is further configured or programmed to control the cartridge spinner to increase the rotational rate of the cartridge to transfer a second part of the fluid from the metering chamber through the valve and to transfer a second remaining part back into the aliquoting chamber. The controller is further configured or programmed to control the measurement system to perform the measurement using the measurement structure and using the measurement system.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which:

FIG. 8 further illustrates part of a method of performing a dispensing fluid using the fluidic elements of FIG. 1;

FIG. 9 further illustrates part of a method of performing a dispensing fluid using the fluidic elements of FIG. 1;

FIG. 10 further illustrates part of a method of performing a dispensing fluid using the fluidic elements of FIG. 1;

DETAILED DESCRIPTION

Like numbered elements in these figures are either equivalent elements or perform the same function. Elements which have been discussed previously will not necessarily be discussed in later figures if the function is equivalent.

For heterogeneous immunochemical assays a washing buffer is often required to perform separation or washing steps to increase test sensitivity and reproducibility. For clinical chemistry tests buffers are often required for sample dilution or biochemical reactions. According to Richtlinie der Bundesärztekammer (RiliBÄK) guidelines for Point of Care (POC) disposables all liquid reagents have to be pre-stored on the disposable. From such pre-storage containers, the released fluid volume is typically released at once. If the fluid volume has to be split into aliquots complicated space-consuming microfluidic structures are required. This space consumption often hinders the implementation of parallel microfluidic structure for panels into microfluidic disposables.

Further, valves typically used for disc format disposables like siphons, geometrical valves or hydrophobic valves can either be used one time only or special variants of siphons can be used several times but a fluid volume in the interconnected chamber is completely transferred through the valve without the possibility to split the volumes into aliquots. Therefore with state-of-the art valves it is not possible to release a fluid volume from a pre-storage containment into a microfluidic cavity featuring a siphon valve and split this volume into several aliquots.

A disadvantage with geometrical valves is that there is no control of fluids with decreased surface tension is possible. This is especially true for washing buffers.

A disadvantage with using hydrophobic valves is that there no control of fluids with decreased surface tension is possible. This is especially true for washing buffers. Hydrophobic valves also have the disadvantage that they can only be used once.

A disadvantage of state of the art siphons is that state of the art siphons can only be filled once. Air bubbles remaining in the siphon after this has been used inhibit a second filling of the siphon. Further the siphons will transfer the complete fluid volume located radially inwards of the siphon from an upstream chamber into a downstream fluidic element.

Figure 1:
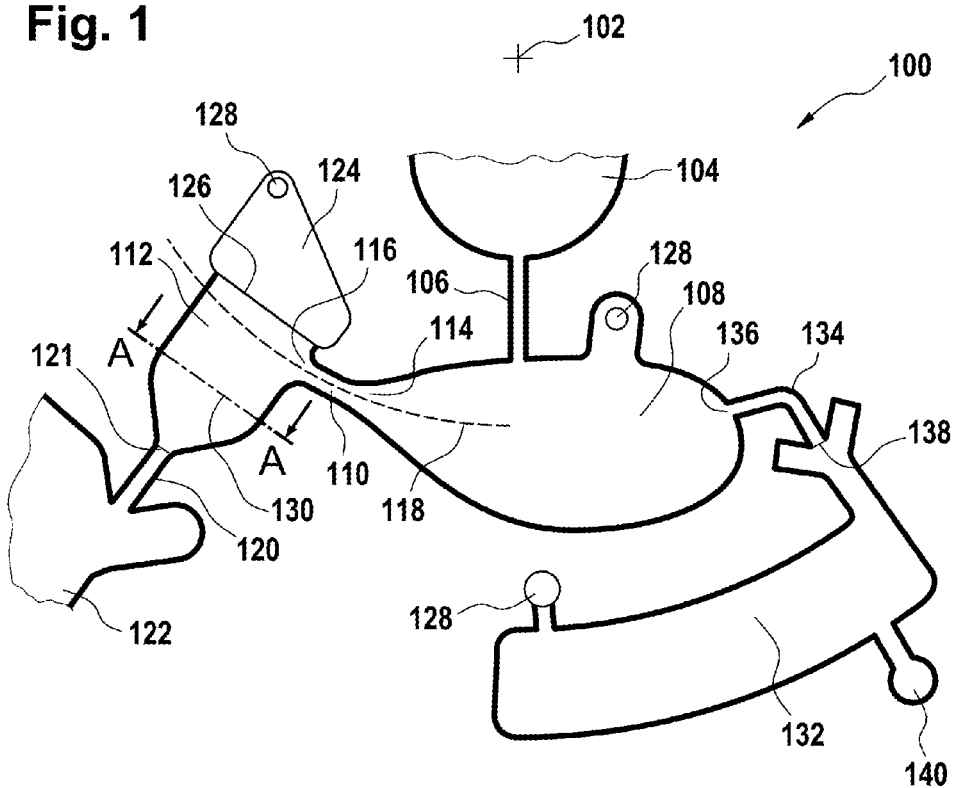
FIG. 1 illustrates fluidic elements for performing multiple aliquots of a fluid.

FIG. 1 shows a number of fluidic components 100. The fluidic components 100 are part of the fluidic components that make up a disc. There is a rotational axis labeled 102. Also shown in the Fig. is a portion of a fluid chamber 104. The fluid chamber either is designed for receiving fluid or for having a reservoir that provides fluid via a fluid chamber duct 106 that leads into the aliquoting chamber 108. In this example the aliquoting chamber 108 is well-shaped. There is a connecting duct 110 which connects the aliquoting chamber 108 with a metering chamber 112. The connecting duct 110 has a duct entrance 114 and a duct exit 116. The duct entrance 114 leads to the aliquoting chamber 108 and the duct exit 116 leads to the metering chamber 112. A circular arc 118 that is drawn about the rotational axis 102 passes both through the duct entrance 114 and the duct exit 116. The metering chamber 112 is connected via a tube 120 to a downstream fluidic element 122. In this example there is a valve 121 between the tube 120 and the metering chamber 112. In this example the valve 121 is a capillary valve.

The valve 121 could be implemented in different ways. In some alternatives the tube 120 could function as a capillary valve. Alternatively a valve could be placed between the elements 120 and 122. In other embodiments a duct could be connected in the same location and a controllable microvalve could be used instead. The controllable microvalve could be placed between the metering chamber 112 and the tube 120 or between the tube 120 and the downstream fluidic element 122.

Figure 2:
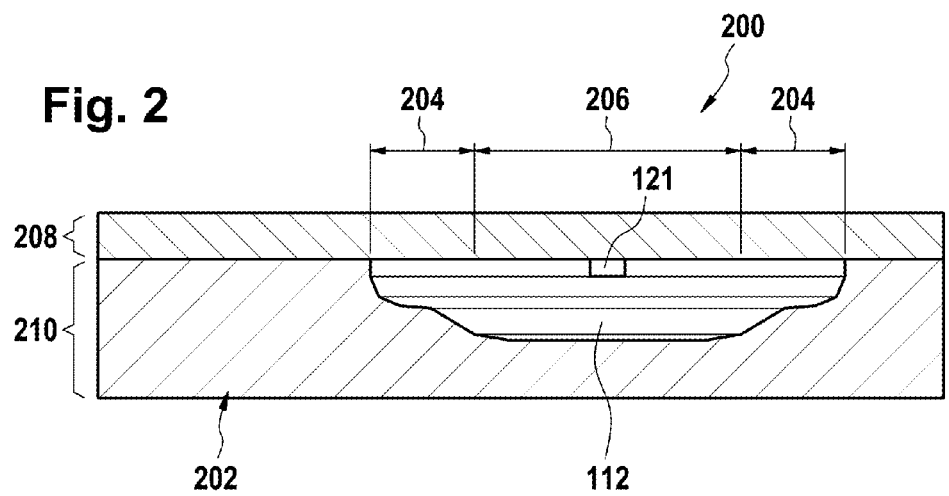
FIG. 2 illustrates a cross sectional view of a metering chamber.

An optional expansion chamber 124 is shown as bordering on an upper edge 126 of the metering chamber 112. There is a vent 128 which vents the expansion chamber 124. The whole boundary between the metering chamber 112 and the expansion chamber 124 is open. This may help reduce the chances of bubbles forming in the metering chamber 112. In some examples the expansion chamber 124 may have a thickness which is greater than that of the metering chamber 112. Capillary forces may be used then to keep the fluid in the metering chamber 112. The dashed line labeled 130 and also A-A shows the location of a cross-sectional view of the metering chamber 112. This cross-sectional view is shown in FIG. 2. The aliquoting chamber 108 can be shown as also having a vent 128. The region around the duct entrance 114 is in this embodiment funnel-shaped. It may also be noted that the aliquoting chamber 108 is shown as not having sharp edges. The lack of sharp edges helps to facilitate the movement of fluid from the aliquoting chamber 108 to the duct entrance 114 when the disc is decelerated.

The aliquoting chamber 108 is also shown as having a connection to a fluidic connection 134 which leads to an excess fluid chamber 132. The fluidic connection 134 has a fluidic connection entrance 136. The fluidic connection entrance 136 defines the maximum fluid level in the aliquoting chamber 108. The maximum fluid level in the aliquoting chamber 108 is lower than the circular arc 118. The fluidic connection 134 is connected to the excess fluid chamber 132 via a capillary valve 138 in this embodiment. The use of a valve or a capillary valve is optional. The excess fluid chamber is shown as having a vent 128 and it is also connected to a failsafe chamber 140. When the fluid flows into the excess fluid chamber 132 the failsafe chamber 140 is filled. The failsafe chamber 140 may be used to indicate if fluid has entered the excess fluid chamber 132 optically. For example during use if the failsafe chamber 140 is not filled it may indicate that the aliquoting chamber 108 was not properly filled with fluid.

FIG. 2 shows a cross-sectional view 200 of the profile A-A which is labeled 130 in FIG. 1. In this Fig. the body of the cartridge 202 can be seen. There is an opening in the body 202 for the metering chamber 112. The body of the cartridge 202 in this example is fabricated by injection molding. The body of the cartridge is assembled from a lid 208 and a support structure 210.

At the far end of the metering chamber the entrance into the valve 121 can be seen. The metering chamber 112 can be seen as being divided into several different regions. On the edges there are two sidewalls regions 204. Between the two sidewalls regions or two side regions is a central region 206. The sidewall 204 regions become more narrow or taper away from the central region 206. This causes a narrowing in the dimensions of the metering chamber 112 in this region. The capillary action may therefore be higher in the sidewall regions 204 than in the central region 206. This may cause the metering chamber 112 to fill with fluid first in the sidewall region before the central region 206. This may have the benefit of using a number of bubbles which are formed or trapped in the metering chamber 112 when the metering chamber 112 is filled with fluid.

Figure 3:
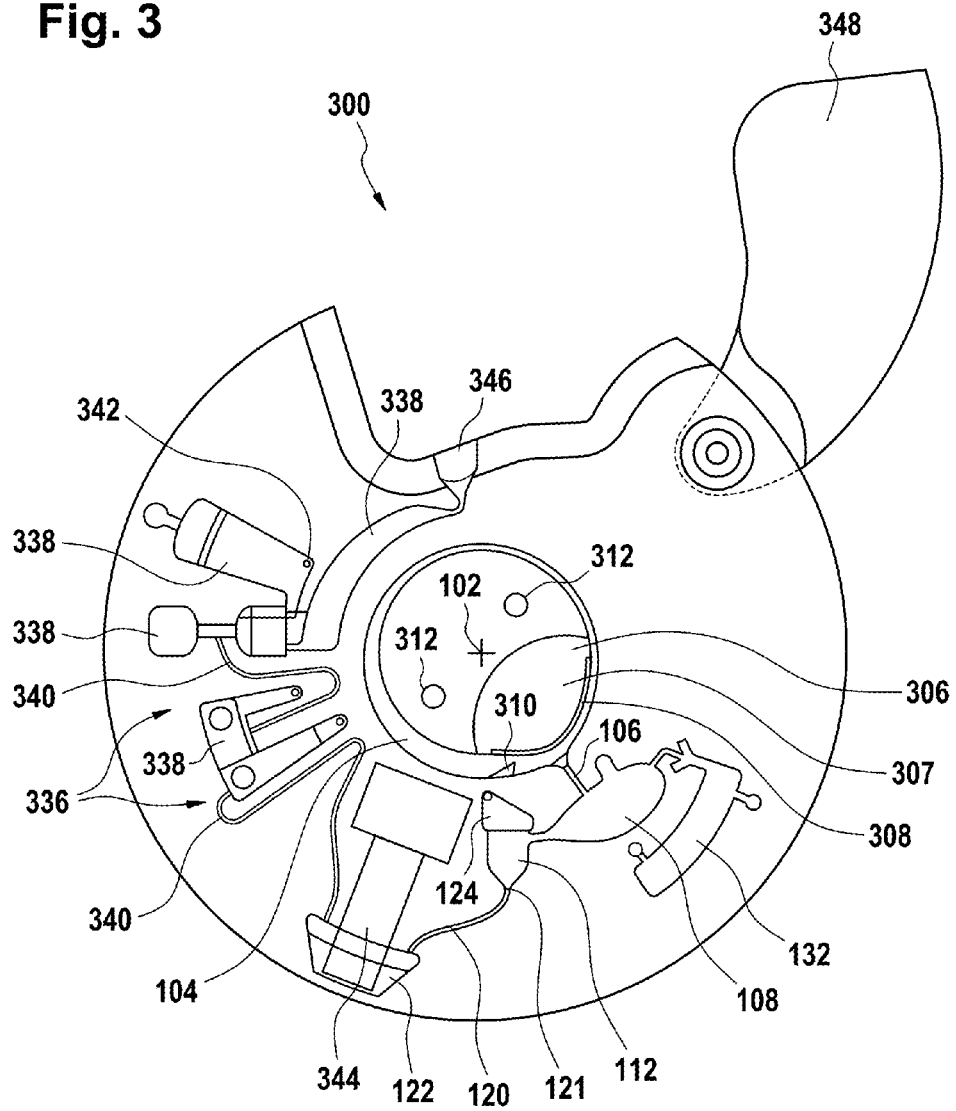
FIG. 3 illustrates an example of a cartridge that incorporates the fluidic elements of FIG. 1.

FIG. 3 shows the integration of the fluidic components 100 into a cartridge 300. The cartridge 300 is flat and disc-like and is shown as having a rotational axis 102. There is a fluid chamber 104 which is adapted or operable for receiving a fluid. The fluid reservoir 306 filled with a fluid 307 is sealed with a pierceable seal 308 in this example and there is a piercing element 310 on the wall of the fluid chamber 104. The fluid reservoir has a number of engaging surfaces or reservoir opening elements 312 which may be manipulated manually or by an apparatus such as an actuator which causes the pierceable seal 308 to contact the piercing element 310. This then causes the fluid chamber 104 to fill with the fluid 307. The fluid chamber 104 is shown as being connected to a first duct 106. The first duct 106 is connected to an aliquoting chamber 108. When the disc 300 is rotated about the rotational axis 102 centrifugal force forces fluid 307 through the duct 106. This then causes the aliquoting chamber 108 to fill with the fluid 307.

The aliquoting chamber 108 is shown as being connected to second duct 110 which leads to the metering chamber 112 as is shown in FIG. 1. In this example the aliquoting chamber 108 is laid out in a plane-like fashion aligned with the plane of the disc. The rotational axis is perpendicular to the plane. Attached to the aliquoting chamber 108 is an excess fluid container 132. This is an optional element.

The metering chamber 112 is shown as being connected to a downstream fluidic element 122 via a tube 120. A valve 121 is positioned between the metering chamber 112 and the tube 120. The downstream fluidic element 122 is part of a fluidic structure 336 for processing a biological sample into a processed biological sample.

The fluidic structure 336 comprises a number of fluidic elements 338 that are connected by various ducts and siphons 340. There are also a number of vents 342 within the fluidic structure 336. In this example there is an opening 346 which enables a biological sample to be placed into the fluidic structure 336. There is also a cover lid 348 which is used to close and seal the opening 346. The fluidic structure 336 also comprises a measurement structure 344 which allows a measurement to be made on the biological sample using a measurement system.

The measurement system may for instance be an optical, electrical, or a combination of the two system for making the measurement on the processed biological sample.

The processing of the biological sample can be controlled by controlling the rotational rate about the rotational axis and duration. The siphons 340 are designed to be filled automatically using a capillary action. However, a sufficiently large rotational rate about the rotational axis 102 will produce a centrifugal force which will oppose the capillary action. Thus, by controlling the rotational rate and the duration of rotation at particular rates the processing of the biological sample can be controlled. In a typical usage the biological sample may be placed into the inlet 346 and the rotation rate of the system may be controlled. Then at some point an actuator or other mechanical means is used to manipulate the reservoir opening element and causes the piercing element 310 to pierce the pierceable seal 308. Rotation can then force fluid into the aliquoting chamber and a variety of rotational rates may be used to perform multiple aliquotations using the cartridge 300.

FIGS. 4-10 illustrate how the fluidic components 100 may be used to perform multiple aliquotations of fluid to the downstream fluidic element 122.

Figure 4:
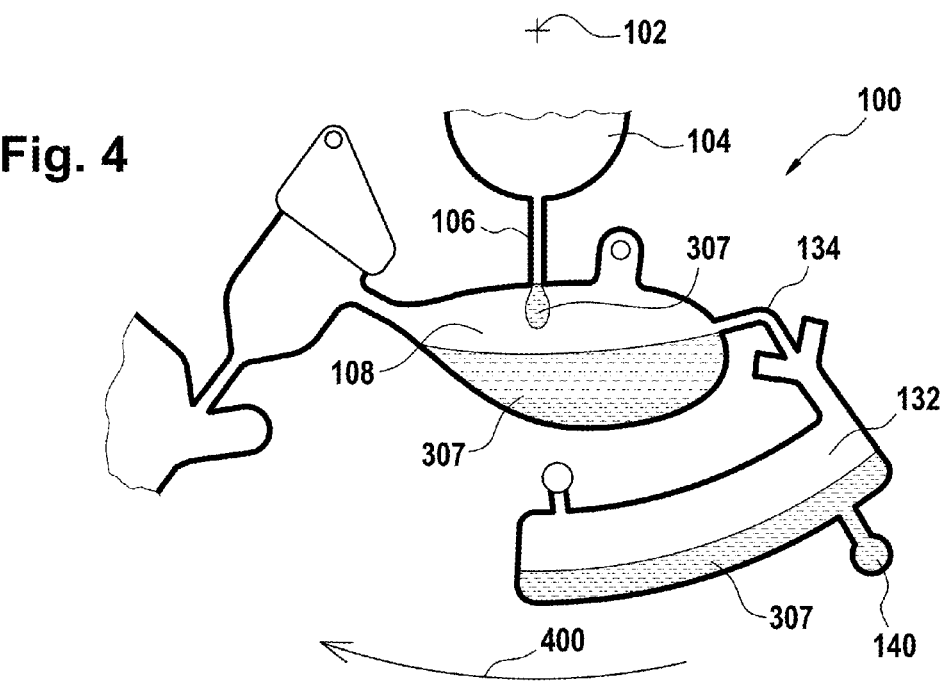
FIG. 4 illustrates part of a method of performing a dispensing fluid using the fluidic elements of FIG. 1.

In FIG. 4 the disc is rotated about the axis of rotation 102 in the direction indicated by the arrow 400. The arrow 400 indicates the direction of rotation. In this particular example the disc is spinning at 20 Hz. Fluid is transported into the aliquoting chamber 108 from the fluid chamber 104. Fluid 307 can be seen dripping from the fluid chamber duct 106 into the aliquoting chamber 108. The fluid volume in the aliquoting chamber 108 is limited and thereby metered by the fluidic connection 134 which connects to the excess fluid chamber 132. The failsafe chamber 140 can be seen as being filled with fluid.

Figure 5:
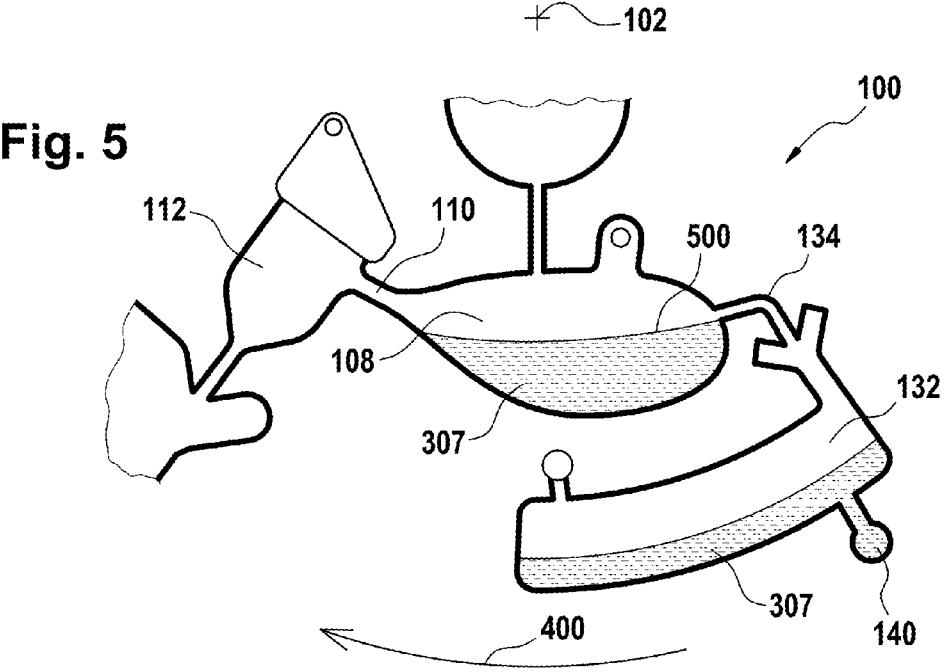
FIG. 5 further illustrates part of a method of performing a dispensing fluid using the fluidic elements of FIG. 1.

Next in FIG. 5 the fluid volume 307 has been completely transferred from the fluid chamber 104 into the aliquoting chamber 108. The failsafe chamber 140 is shown as being filled with the fluid. In this example the disc is still spinning at the same rate as was shown in FIG. 4. The aliquoting chamber 108 is filled with fluid 307 up to the maximum fluid level 500. It can be seen that the maximum fluid level 500 is below or further away from the axis of rotation 102 than the connecting duct 110. When the disc is spinning in this way the fluid 307 cannot enter the metering chamber 112.

Figure 6:
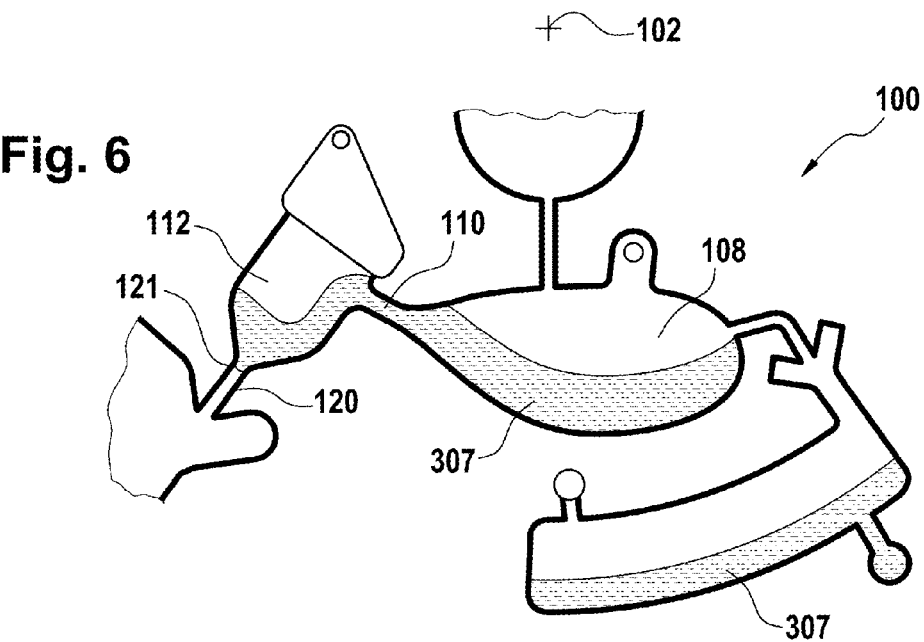
FIG. 6 further illustrates part of a method of performing a dispensing fluid using the fluidic elements of FIG. 1.

Next in FIG. 6 the disc stops with a high rate of deceleration for example at 50 Hz per second. The inertia of the fluid forces the fluid 307 towards and through the connecting duct 110 and into the metering chamber 112. It can be seen in this Fig. that the fluid 307 is filling the sides of the metering chamber 112 before it is filling the central region. This is because of the tapered like structures 204 shown in FIG. 2. Capillary action causes this portion of the metering chamber 112 to fill first. This manner of filling the metering chamber may reduce the chances that air bubbles form or adhere in the metering chamber 112.

Figure 7:
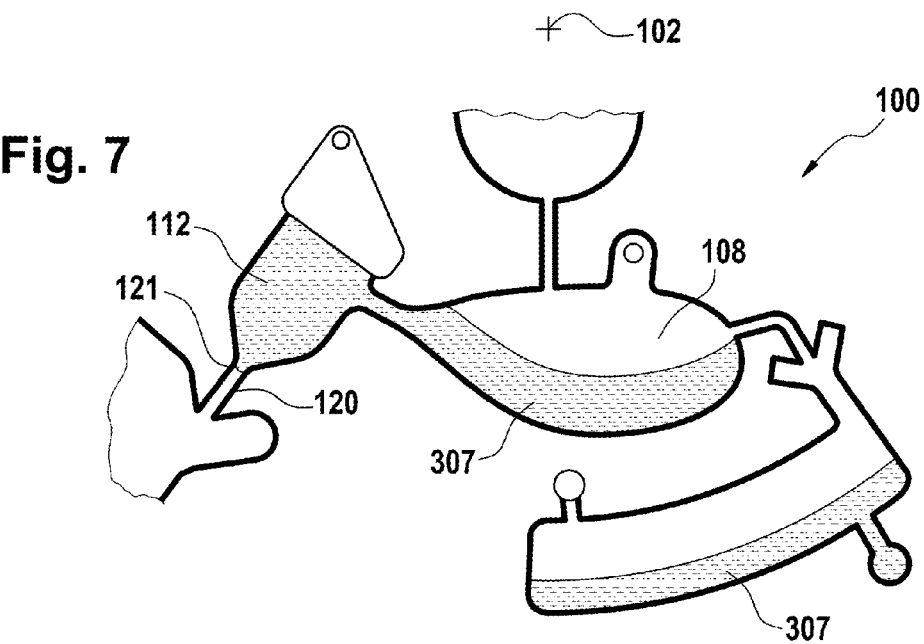
FIG. 7 further illustrates part of a method of performing a dispensing fluid using the fluidic elements of FIG. 1.

In FIG. 7 the cartridge is still stationary or at a reduced rotation rate and the metering chamber 112 is completely filled with fluid 307. The cartridge or disc may still be considered to be at rest. The complete filling of the metering chamber is caused by capillary forces caused by the respective geometrical dimensions of the metering chamber.

FIG. 8 shows the same view as is shown in FIG. 7 except a dashed line 800 has been drawn in the metering chamber 112. This line 800 in the metering chamber 112 divides the fluid in the metering chamber into several parts or portions. The fluid part 804 radially inward (closer to axis of rotation 102) from the line 800 may flow back into the reservoir. The radially outward part (further from the axis of rotation 102) or part 802 may be completely transferred into the fluidic element 122. The radially inward part 804 can be referred to as the remaining part of the fluid and the radially outward part 802 can be referred to as the part of the fluid 802 that is transferred into the downstream fluidic element. The volume of the fluid 802 is the aliquot transferred in a subsequent step to the downstream fluidic element 122

Next in FIG. 9 the disc begins to accelerate and spin around in the direction 400. The disc for instance may spin at the rate shown in FIGS. 1 and 2. The disc accelerates; this causes the capillary valve 121 to open. The remaining part of the fluid 804 was transferred back to the aliquoting chamber 108. The part of the fluid 802 is in the process of being transferred to the downstream fluidic element 122. A drop of the fluid can be seen dropping from the tube 120.

Next in FIG. 10 it can be seen that the fluid volume 802 has been completely transferred to the downstream fluidic element 122 and is no longer visible in the Fig. The remaining part of the fluid 804 has been transferred into the aliquoting chamber 108 and is mixed with the fluid 307. The first aliquotion step is finished; the process may be repeated again from FIG. 6 and may be repeated until the fluid volume 307 in the aliquoting chamber 108 is smaller than the volume of the metering chamber 112.

Figure 11:
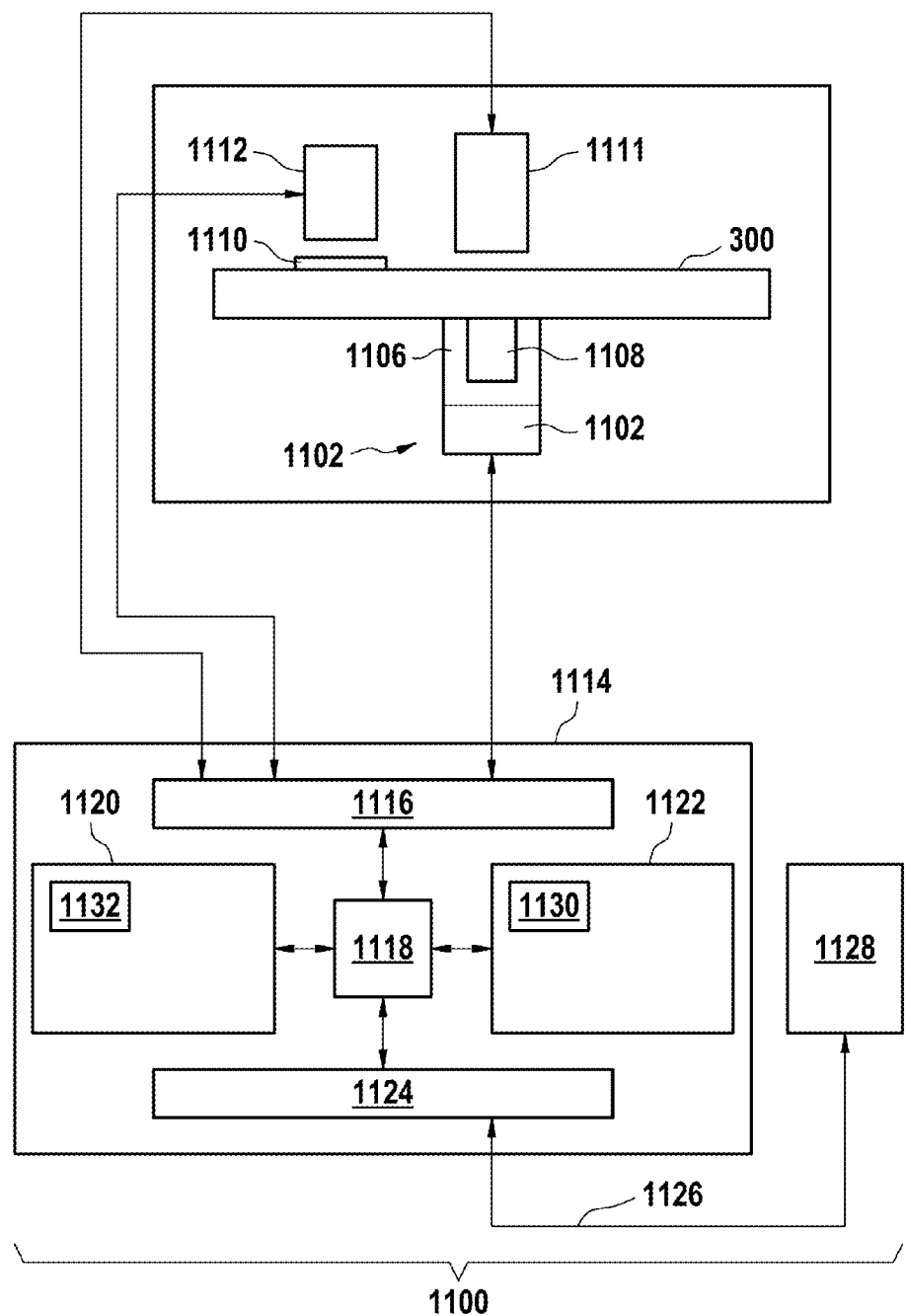
FIG. 11 illustrates an example of an automatic analyzer.

FIG. 11 shows an example of an automatic analyzer. The automatic analyzer 1100 is adapted for receiving a cartridge 300. There is a cartridge spinner 1102 which is operable for rotating the cartridge 300 about the rotational axis 102. The cartridge spinner 1102 has a motor 1104 attached to a gripper 1106 which attaches to a portion of the cartridge 1108. The cartridge 300 is shown further as having a measurement or transparent structure 1110. The cartridge 300 can be rotated such that the measurement structure 1110 goes in front of a measurement system 1112 which can perform for example an optical measurement on the processed biological sample. The actuator 1104 as was shown previously is also shown in this FIG. 1t can be used to open a fluid reservoirs in the cartridge 100. In some examples the actuator may be replaced with a dispenser with a dosing needle for filling the fluid chamber of the cartridge 300.

The actuator 1111, the cartridge spinner 1102, and the measurement system 1112 are shown as all being connected to a hardware interface 1116 of a controller 1114. The controller 1114 contains a processor 1118 in communication with the hardware interface 1116, electronic storage 1120, electronic memory 1122, and a network interface 1124. The electronic memory 1130 has a machine executable instructions which enables the processor 1118 to control the operation and function of the automatic analyzer 1100. The electronic storage 1120 is shown as containing a measurement 1132 that was acquired when instructions 1130 were executed by the processor 1118. The network interface 1124 enables the processor 1118 to send the measurement 1132 via network interface 1126 to a laboratory information system 1128.

Figure 12:
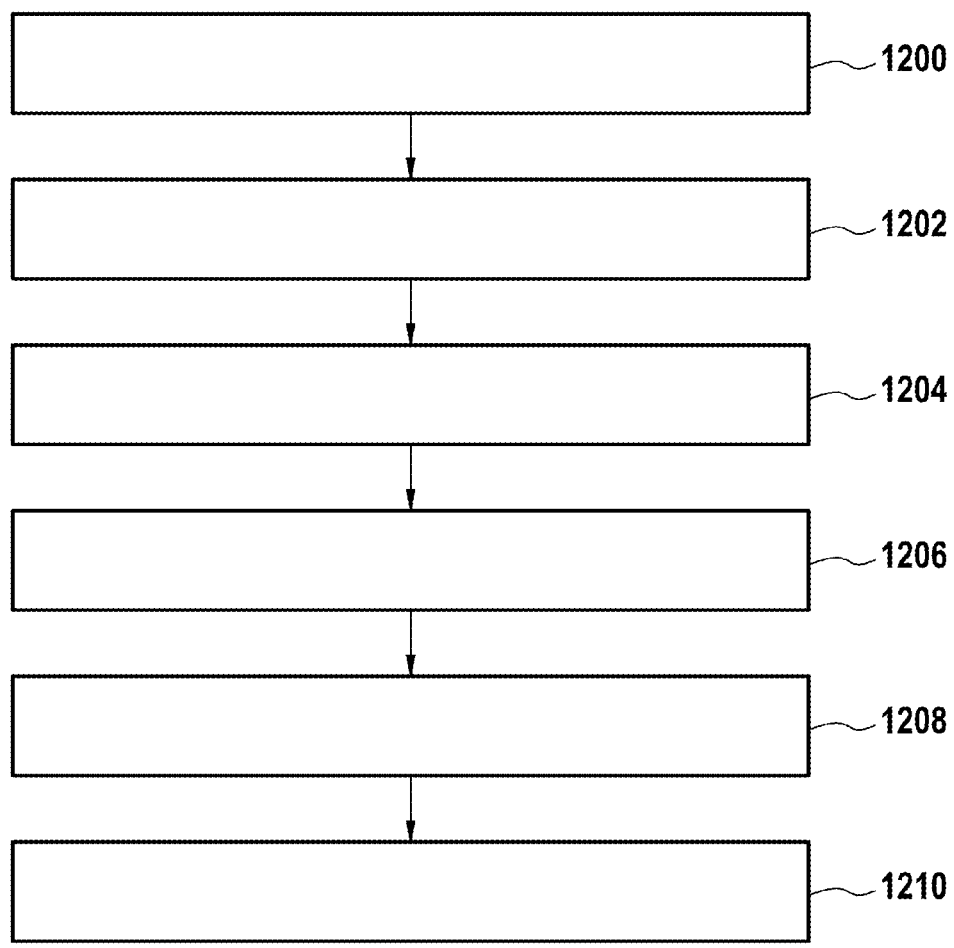
FIG. 12 shows a flow chart which illustrates a method of operating the automatic analyzer of FIG. 11.

FIG. 12 shows a flowchart which illustrates a method of operating the automatic analyzer 1100 shown in FIG. 11. First in step 1200 the processor 118 controls the cartridge spinner 1102 to control the rotational rate of the cartridge to process the biological sample into the processed biological sample using the fluidic structure. Next in step 1202 the processor 1108 controls the cartridge spinner 1102 to decrease the rotational rate of the cartridge to force fluid in the aliquoting chamber into the connecting duct and to fill the metering chamber 112 for a first time. Next in step 1204 the processor 1108 controls the cartridge spinner 1102 to increase the rotational rate of the cartridge 300 to transfer a first part of the fluid from the metering chamber through the valve and to transfer a first remaining part back into the aliquoting chamber 108. Next in step 1206 the processor controls the cartridge spinner to increase the rotational rate of the cartridge to force the fluid in the reservoir into the connecting duct 110 and to fill the metering chamber 112 a second time. Next the processor controls the cartridge spinner to increase the rotational rate of the cartridge 300 to transfer a second part of the fluid from the metering chamber through the valve and to transfer a second remaining part back into the aliquoting chamber. Finally in step 1210 the processor controls the measurement system 112 to perform the measurement in the measurement structure 110.

LIST OF REFERENCE NUMERALS 100 fluidic components
102 rotational axis
104 fluid chamber
106 fluid chamber duct
108 aliquoting chamber
110 connecting duct
112 metering chamber
114 duct entrance
116 duct exit
118 circular arc
120 tube
121 valve
122 downstream fluidic element
124 expansion chamber
126 upper edge
128 vent
130 profile A-A
132 excess fluid chamber
134 fluidic connection
136 fluidic connection entrance
138 capillary valve
140 fail safe chamber
200 cross sectional view A-A
202 body of cartridge
204 side walls
206 central region
208 lid
210 support structure
300 cartridge
306 fluid reservoir with fluid
307 fluid
308 pierceable seal
310 piercing element
312 engaging surface or reservoir opening element
336 fluidic structure
338 fluidic element 340 siphon
342 vent
344 measurement structure
346 opening
348 cover lid
400 direction of rotation
500 maximum fluid level
800 dividing line
802 part of fluid
804 remaining part of fluid
1100 automatic analyzer
1102 cartridge spinner
1104 motor
1106 gripper
1108 portion of cartridge
1110 measurement structure
1111 actuator
1112 measurement system
1114 controller
1116 hardware interface
1118 processor
1120 electronic storage
1122 electronic memory
1124 network interface
1126 network connection
1128 laboratory information system
1130 executable instructions
1132 measurement
1200 control the rotational rate of the cartridge to process the biological sample into the processed biological sample using the fluidic structure
1202 decrease the rotational rate of the cartridge to force the fluid in the aliquoting chamber into the connecting duct and to fill the metering chamber a first time
1204 increasing the rotational rate of the cartridge to transfer a first part of the fluid from the metering chamber through the valve and to transfer a first remaining part back into the aliquoting chamber
1206 decrease the rotational rate of the cartridge to force the fluid in the aliquoting chamber into the connecting duct and to fill the metering chamber a second time
1208 increase the rotational rate of the cartridge to transfer a second part of the fluid from the metering chamber through the valve and to transfer a second remaining part back into the aliquoting chamber
1210 control the measurement system to perform the measurement using the measurement structure and using a measurement system

What is claimed is:

1. A method of performing a measurement of a processed biological sample using a cartridge, wherein the cartridge is operable for being spun around a rotational axis, wherein the cartridge comprises:
an aliquoting chamber;
a metering chamber, wherein the metering chamber has side wall regions and a central region, wherein the side wall regions are narrower than the central region in a cross sectional view of the metering chamber, wherein capillary action next to the side wall regions of the metering chamber is greater than in the central region of the metering chamber,
a connecting duct for connecting the metering chamber with the aliquoting chamber, wherein the connecting duct comprises a duct entrance in the aliquoting chamber, wherein the connecting duct further comprises a duct exit in the metering chamber, wherein a circular arc about the rotational axis passes through both the duct entrance and the duct exit;
a downstream fluidic element, wherein the downstream fluidic element is connected to the metering chamber via a valve;
a fluidic structure for processing a biological sample into the processed biological sample, wherein the fluidic structure comprises the downstream fluidic element, wherein the downstream fluidic element is fluidically connected to the fluidic structure, wherein the fluidic structure comprises a measurement structure for enabling measurement of the processed biological sample, wherein the fluidic structure is configured for receiving the biological sample;
wherein the method comprises the steps of:
placing the biological sample into the fluidic structure;
controlling the rotational rate of the cartridge to process the biological sample into the processed biological sample using the fluidic structure;
filling the aliquoting chamber with a fluid;
decreasing the rotational rate of the cartridge to permit the fluid in the aliquoting chamber to flow into the connecting duct and to fill the metering chamber a first time;
increasing the rotational rate of the cartridge to transfer a first part of the fluid from the metering chamber through the valve and to transfer a first remaining part back into the aliquoting chamber;
decreasing the rotational rate of the cartridge to permit the fluid in the aliquoting chamber to flow into the metering chamber and to fill the metering chamber a second time;
increasing the rotational rate of the cartridge to transfer a second part of the fluid from the metering chamber through the valve and to transfer a second remaining part back into the aliquoting chamber;
performing the measurement using the measurement structure and using a measurement system; and
a vent, wherein the vent is connected to the metering chamber, wherein the vent is nearer to the rotational axis than the metering chamber.

2. The method of claim 1, wherein the step of increasing the rotational rate of the cartridge to transfer the first part of the fluid from the metering chamber through the valve comprises increasing the rotational rate of the cartridge to a first rotational rate to transfer the first remaining part of the fluid back to the aliquoting chamber and increasing the rotational rate of the cartridge to a second rotational rate to transfer the first part of the fluid from the metering chamber through the valve; and/or wherein the step of increasing the rotational rate of the cartridge to transfer a second part of the fluid from the metering chamber through the valve comprises increasing the rotational rate of the cartridge to the first rotational rate to transfer the second remaining part of the fluid back to the aliquoting chamber and increasing the rotational rate of the cartridge to the second rotational rate to transfer the second part of the fluid from the metering chamber through the valve.

3. The method of claim 1, wherein the cartridge further comprises a fluid chamber for receiving the fluid, wherein the cartridge further comprises a fluid chamber duct connecting the fluid chamber and the aliquoting chamber, wherein filling the aliquoting chamber comprises:
filling the fluid chamber with the fluid; and
controlling the rotational rate of the cartridge to transport the fluid from the fluid chamber to the aliquoting chamber via the fluid chamber duct.

4. The method of claim 1, wherein the cartridge further comprises an excess fluid chamber connected to the aliquoting chamber via a fluidic connection, wherein the fluidic connection comprises a fluidic connection entrance, wherein the fluidic connection entrance is further away from the rotational axis than the circular arc that passes through both the duct entrance and the duct exit.

5. The method of claim 1, wherein the aliquoting chamber has a lower portion and an upper portion, wherein the lower portion is further from the rotational axis than the upper portion, wherein a cross sectional profile of the lower portion tapers away from the upper portion.

6. The method of claim 1, wherein the connecting duct is operable for causing fluid to flow from the aliquoting chamber to the metering chamber using capillary action.

7. The method of claim 1, wherein the areas next to the side wall regions of the metering chamber are operable for filling with the fluid before the central region to prevent the formation and/or adherence of bubbles in the metering chamber.

8. A cartridge for an automatic analyzer, wherein the cartridge is operable for being spun around a rotational axis, wherein the cartridge comprises:
   an aliquoting chamber;
   a metering chamber, wherein the metering chamber has side wall regions and a central region, wherein the side wall regions are narrower than the central region in a cross sectional view, wherein capillary action next to the side wall regions of the metering chamber is greater than in the central region of the metering chamber;
   a connecting duct for connecting the metering chamber with the aliquoting chamber, wherein the connecting duct comprises a duct entrance in the aliquoting chamber, wherein the connecting duct further comprises a duct exit in the metering chamber, wherein a circular arc about the rotational axis passes through both the duct entrance and the duct exit;
   a downstream fluidic element, wherein the downstream fluidic element is connected to the metering chamber via a valve;
   a fluidic structure for processing a biological sample into the processed biological sample, wherein the fluidic structure comprises the downstream fluidic element, wherein the downstream fluidic element is fluidically connected to the fluidic structure, wherein the fluidic structure comprises a measurement structure for enabling measurement of the processed biological sample, wherein the fluidic structure is configured for receiving the biological sample; and
   a vent, wherein the vent is connected to the metering chamber, wherein the vent is nearer to the rotational axis than the metering chamber.

9. The cartridge of claim 8, wherein the cartridge further comprises an excess fluid chamber connected to the aliquoting chamber via a fluidic connection, wherein the fluidic connection comprises a fluidic connection entrance, wherein the fluidic connection entrance is further away from the rotational axis than the circular arc that passes through both the duct entrance and the duct exit.

10. The cartridge of claim 8, wherein the aliquoting chamber has a lower portion and an upper portion, wherein the lower portion is further from the rotational axis than the upper portion, wherein a cross sectional profile of the lower portion tapers away from the upper portion.

11. The cartridge of claim 8, wherein the aliquoting chamber has an aliquoting chamber surface, wherein a part of the aliquoting chamber surface near the duct is rounded.

12. The cartridge of claim 8, wherein the connecting duct is operable for causing fluid to flow from the aliquoting chamber to the metering chamber using capillary action.

13. The cartridge of claim 8, wherein the cartridge further comprises an expansion chamber, wherein the vent is within the expansion chamber, wherein the expansion chamber is connected to the metering chamber, wherein capillary action in the metering chamber is greater than capillary action in the expansion chamber, wherein the expansion chamber is nearer to the rotational axis than the metering chamber.

14. The cartridge of claim 8 wherein the cartridge further comprises:
   a fluid chamber for receiving a fluid; and
   a fluid chamber duct connecting the fluid chamber and the aliquoting chamber.

15. The cartridge of claim 8, wherein the measurement structure comprises two or more electrodes and/or an optical measurement structure.

16. An automatic analyzer configured for receiving a cartridge according to claim 8, wherein the automatic analyzer comprises a cartridge spinner, a measurement system, and a controller configured to control the automatic analyzer, wherein the controller is configured to:
   control the cartridge spinner to control the rotational rate of the cartridge to process the biological sample into the processed biological sample using the fluidic structure;
   control the cartridge spinner to decrease the rotational rate of the cartridge to permit the fluid in the reservoir into the connecting duct and to fill the metering chamber a first time;
   control the cartridge spinner to increasing the rotational rate of the cartridge to transfer a first part of the fluid from the metering chamber through the valve and to transfer a first remaining part back into the aliquoting chamber;
   control the cartridge spinner to decrease the rotational rate of the cartridge to permit the fluid in the reservoir into the connecting duct and to fill the metering chamber a second time;
   control the cartridge spinner to increase the rotational rate of the cartridge to transfer a second part of the fluid from the metering chamber through the valve and to transfer a second remaining part back into the aliquoting chamber; and
   control the measurement system to perform the measurement using the measurement structure and using a measurement system.

* * * * *